US006953670B2

(12) United States Patent
Snodgrass et al.

(10) Patent No.: US 6,953,670 B2
(45) Date of Patent: Oct. 11, 2005

(54) METHODS FOR IDENTIFYING COMPOUNDS CAPABLE OF SUPPLEMENTING THE BIOLOGICAL ACTIVITY OF LEPTIN

(75) Inventors: H. Ralph Snodgrass, Powell, OH (US); Joseph Cioffi, New Albany, OH (US); Thomas Joel Zupancic, Worthington, OH (US); Alan Wayne Shafer, Lancaster, OH (US)

(73) Assignee: Indevus Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 10/245,616

(22) Filed: Sep. 17, 2002

(65) Prior Publication Data

US 2003/0082612 A1 May 1, 2003

Related U.S. Application Data

(60) Division of application No. 08/588,189, filed on Jan. 18, 1996, now Pat. No. 6,451,523, which is a continuation-in-part of application No. 08/355,888, filed on Dec. 14, 1994, now Pat. No. 5,763,211, which is a continuation-in-part of application No. 08/306,231, filed on Sep. 14, 1994, now Pat. No. 5,643,748.

(51) Int. Cl.$^7$ ............................................. G01N 33/53

(52) U.S. Cl. ..................... 435/7.9; 435/7.21; 435/7.1; 530/350; 536/23.5

(58) Field of Search ....................... 530/350; 536/23.5; 435/7.21, 7.9, 7.1

(56) References Cited

FOREIGN PATENT DOCUMENTS

| EP | 0 409 607 A2 | 1/1991 |
| EP | 0 521 156 A1 | 1/1993 |
| WO | WO 88/02757 | 4/1988 |
| WO | WO 93/10151 | 5/1993 |
| WO | WO 96/07737 | 3/1996 |

OTHER PUBLICATIONS

Bahary et al., 1990, "Molecular Mapping of the Mouse db Mutation," Proc. Natl. Acad. Sci. U.S.A. 87:8642–8646.
Bazan, 1990, "Structural Design and Molecular Evolution of a Cytokine Receptor Superfamily," Proc. Natl. Acad. Sci. U.S.A. 87:6934–6938.
Beckmann et al., 1994, "Molecular characterization of a family of ligands for eph–related tyrosine kinase receptors," The EMBO Journal 13(16):3757–3762.
Chua, et al., 1996, "Phenotypes of Mouse diabetes and Rat fatty Due to Mutations in the OB (Leptin) Receptor," Science 271:994–996.
Cioffi et al., 1996, "Novel B219/OB Receptor Isoforms: Possible Roles of Leptin in Hematopoiesis and Reproduction," Nature Medicine 2(5):585–589.

Cosman et al., 1990, "A new Cytokine Receptor Superfamily," TIBS 15:265–269.
Dusanter–Fourt et al., 1994, "Transduction du Signal Par Les Recepteurs De Cytokines," Medecine Sciences 10:825–835.
Fukunaga et al., 1990, "Expression Cloning of a Receptor for Murine Granulocyte Colony–Stimulating Factor," Cell 61:341–350.
Gearing et al., 1987, "Molecular Cloning and Expression of cDNA Encoding a Murine Myeloid Leukaemia Inhibitory Factor (LIF)," The EMBO Journal 6:3995–4002.
Gearing et al., 1989, "Expression cloning of a receptor for human granulocyte–macrophage colony–stimulating factor," The EMBO Journal 8(12):3667–3676.
Gorman et al., 1990, "Cloning and Expression of a Gene Encoding an Interleukin 3 receptor–Like Protein: Identification of Another Member of the Cytokine Receptor Gene Family," Proc. Natl. Acad. Sci. U.S.A. 87:5459–5463.
Harada et al., 1990, "Expression Cloning of a cDNA Encoding the Murine Interleukin 4 Receptor Based on Ligand Binding," Proc. Natl. Acad. Sci. U.S.A. 87:857–861.
Hayashida et al., 1990, "Molecular cloning of a second subunit of the receptor for human granulocyte–macrophage colony–stimulating factor (GM–CSF): Reconstitution of a high–affinity GM–CSF receptor," Proc. Natl. Acad. Sci. U.S.A. 87:9655–9659.
Hibi et al., 1990, "Molecular Cloning and Expression of a Il–6 Signal Transducer, gp130," Cell 63:1149–1157.
Jacobs et al. 1985 "Isolation and characterization of genomic and cDNA clones of human erythropoietin." Nature 313(6005):806–10.
Larsen et al., 1990, "Expression Cloning of a Human Granulocyte Colony–stimulating Factor Receptor: A Structural Mosaic of Hematopoietin Receptor, Immunoglobulin, and Fibronectin Domains," J. Exp. Med. 172:1559–1570.
Miyajima et al., 1992, "Cytokine Receptors and Signal Transduction," Ann. Rev. Immunol. 10:295–331.
Miyajima et al., 1993, "Receptors for Granulocyte–Macrophage Colony–Stimulating Factor, Interleukin–3, and Interleukin–5," Blood 82(7):1960–1974.

(Continued)

*Primary Examiner*—Elizabeth Kemmerer
*Assistant Examiner*—Eileen B. O'Hara
(74) *Attorney, Agent, or Firm*—Jones Day

(57) ABSTRACT

The present invention relates to a variant from of the receptor for the obese gene product. In particular, the invention relates to methods of detecting this receptor variant in cells and tissues of obese individuals. In addition, it relates to methods of inhibiting or down regulating expression of this variant in cells to augment their responsiveness to weight regulation by leptin as well as methods of using compounds to directly activate signal transduction pathways associated with this ligand-receptor system. In addition, the invention relates to identifying compounds capable of supplementing biological activity of leptin on cells expressing a leptin receptor variant.

11 Claims, 7 Drawing Sheets

OTHER PUBLICATIONS

Mosley et al., 1989, "The Murine Interleukin–4 Receptor: Molecular Cloning and Characterization of Secreted and Membrane Bound Forms," Cell 59:335–348.

Ono et al., 1987 "A Novel Human Nonviral Retroposon Derived From An Endogenous Retrovirus", Nuc. Acid. Res. 15:8725–8737.

Park et al., 1992, "Cloning of the low–affinity murine granulocyte–macrophage colony–stimulating factor receptor and reconstitution of a high–affinity receptor complex," Proc. Natl. Acad. Sci. U.S.A. 89:4295–4299.

Pelleymounter et al., 1995, "Effects of the obese Gene Product on Body Weight Regulation in ob/ob Mice," Science 269:540–549.

Saito et al., 1992, "Molecular Cloning of a Murine IL–6 Receptor–Associated Signal Transducer, gp130, and its Regulated Expression in Vivo," J. Immunol. 148(12):4066–4071.

Seed et al., 1987 "Molecular cloning of the CD2 antigen, The T–cell erythrocyte receptor, by a rapid immunoselection procedure." Proc Natl Acad Sci U S A. 84(10):3365–9.

Singer, 1982, "SINEs And LINEs: Highly Repeated Short And Long Interspersed Sequences In Mammalian Genomes", Cell 28:433–434.

Tartaglia et al., 1995, "Identification and expression cloning of a leptin receptor, OB–R" Cell 83(7):1263–1271.

Truett et al., 1991, "Rat Obesity Gene fatty (fa) Mapps to Chromosome 5: Evidence for Homology with the Mouse Gene diabetes (db)," Proc. Natl. Acad. Sci. U.S.A. 88:7806–7809.

Wong et al. 1985 "Human GM–CSF: molecular cloning of the complementary DNA and purification of the natural and recombinant proteins." Science. 17;228(4701):810–5.

Yamasaki et al., 1988, "Cloning and Expression of the Human Interleukin–6 (BSF–2/IFNβ 2) Receptor," Science 241:825–828.

```
              9           18          27          36          45          54
GCG CGC GCG ACG CAG GTG CCC GAG CCC CGG CCC GCG CCC ATC TCT GCC TTC GGT
--- --- --- --- --- --- --- --- --- --- --- --- --- --- --- --- --- ---
 A   R   A   T   Q   V   P   E   P   R   P   A   P   I   S   A   F   G 63          72          81          90          99         108
CGA GTT GGA CCC CCG GAT CAA GGT GTA CTT CTC TGA AGT AAG ATG ATT TGT CAA
--- --- --- --- --- --- --- --- --- --- --- --- --- --- --- --- --- ---
 R   V   G   P   P   D   Q   G   V   L   L   *   S   K   M   I   C   Q 117         126         135         144         153         162
AAA TTC TGT GTG GTT TTG TTA CAT TGG GAA TTT ATT TAT GTG ATA ACT GCG TTT
--- --- --- --- --- --- --- --- --- --- --- --- --- --- --- --- --- ---
 K   F   C   V   V   L   L   H   W   E   F   I   Y   V   I   T   A   F 171         180         189         198         207         216
AAC TTG TCA TAT CCA ATT ACT CCT TGG AGA TTT AAG TTG TCT TGC ATG CCA CCA
--- --- --- --- --- --- --- --- --- --- --- --- --- --- --- --- --- ---
 N   L   S   Y   P   I   T   P   W   R   F   K   L   S   C   M   P   P 225         234         243         252         261         270
AAT TCA ACC TAT GAC TAC TTC CTT TTG CCT GCT GGA CTC TCA AAG AAT ACT TCA
--- --- --- --- --- --- --- --- --- --- --- --- --- --- --- --- --- ---
 N   S   T   Y   D   Y   F   L   L   P   A   G   L   S   K   N   T   S 279         288         297         306         315         324
AAT TCG AAT GGA CAT TAT GAG ACA GCT GTT GAA CCT AAG TTT AAT TCA AGT GGT
--- --- --- --- --- --- --- --- --- --- --- --- --- --- --- --- --- ---
 N   S   N   G   H   Y   E   T   A   V   E   P   K   F   N   S   S   G 333         342         351         360         369         378
ACT CAC TTT TCT AAC TTA TCC AAA GCA ACT TTC CAC TGT TGC TTT CGG AGT GAG
--- --- --- --- --- --- --- --- --- --- --- --- --- --- --- --- --- ---
 T   H   F   S   N   L   S   K   A   T   F   H   C   C   F   R   S   E 387         396         405         414         423         432
CAA GAT AGA AAC TGC TCC TTA TGT GCA GAC AAC ATT GAA GGA AGG ACA TTT GTT
--- --- --- --- --- --- --- --- --- --- --- --- --- --- --- --- --- ---
 Q   D   R   N   C   S   L   C   A   D   N   I   E   G   R   T   F   V
```

FIG.1A

```
     441           450           459           468           477           486
TCA ACA GTA AAT TCT TTA GTT TTT CAA CAA ATA GAT GCA AAC TGG AAC ATA CAG
--- --- --- --- --- --- --- --- --- --- --- --- --- --- --- --- --- ---
 S   T   V   N   S   L   V   F   Q   Q   I   D   A   N   W   N   I   Q 495           504           513           522           531           540
TGC TGG CTA AAA GGA GAC TTA AAA TTA TTC ATC TGT TAT GTG GAG TCA TTA TTT
--- --- --- --- --- --- --- --- --- --- --- --- --- --- --- --- --- ---
 C   W   L   K   G   D   L   K   L   F   I   C   Y   V   E   S   L   F 549           558           567           576           585           594
AAG AAT CTA TTC AGG AAT TAT AAC TAT AAG GTC CAT CTT TTA TAT GTT CTG CCT
--- --- --- --- --- --- --- --- --- --- --- --- --- --- --- --- --- ---
 K   N   L   F   R   N   Y   N   Y   K   V   H   L   L   Y   V   L   P 603           612           621           630           639           648
GAA GTG TTA GAA GAT TCA CCT CTG GTT CCC CAA AAA GGC AGT TTT CAG ATG GTT
--- --- --- --- --- --- --- --- --- --- --- --- --- --- --- --- --- ---
 E   V   L   E   D   S   P   L   V   P   Q   K   G   S   F   Q   M   V 657           666           675           684           693           702
CAC TGC AAT TGC AGT GTT CAT GAA TGT TGT GAA TGT CTT GTG CCT GTG CCA ACA
--- --- --- --- --- --- --- --- --- --- --- --- --- --- --- --- --- ---
 H   C   N   C   S   V   H   E   C   C   E   C   L   V   P   V   P   T 711           720           729           738           747           756
GCC AAA CTC AAC GAC ACT CTC CTT ATG TGT TTG AAA ATC ACA TCT GGT GGA GTA
--- --- --- --- --- --- --- --- --- --- --- --- --- --- --- --- --- ---
 A   K   L   N   D   T   L   L   M   C   L   K   I   T   S   G   G   V 765           774           783           792           801           810
ATT TTC CGG TCA CCT CTA ATG TCA GTT CAG CCC ATA AAT ATG GTG AAG CCT GAT
--- --- --- --- --- --- --- --- --- --- --- --- --- --- --- --- --- ---
 I   F   R   S   P   L   M   S   V   Q   P   I   N   M   V   K   P   D 819           828           837           846           855           864
CCA CCA TTA GGT TTG CAT ATG GAA ATC ACA GAT GAT GGT AAT TTA AAG ATT TCT
--- --- --- --- --- --- --- --- --- --- --- --- --- --- --- --- --- ---
 P   P   L   G   L   H   M   E   I   T   D   D   G   N   L   K   I   S
```

FIG. 1B

```
      873         882         891         900         909         918
TGG TCC AGC CCA CCA TTG GTA CCA TTT CCA CTT CAA TAT CAA GTG AAA TAT TCA
--- --- --- --- --- --- --- --- --- --- --- --- --- --- --- --- --- ---
 W   S   S   P   P   L   V   P   F   P   L   Q   Y   Q   V   K   Y   S 927         936         945         954         963         972
GAG AAT TCT ACA ACA GTT ATC AGA GAA GCT GAC AAG ATT GTC TCA GCT ACA TCC
--- --- --- --- --- --- --- --- --- --- --- --- --- --- --- --- --- ---
 E   N   S   T   T   V   I   R   E   A   D   K   I   V   S   A   T   S 981         990         999        1008        1017        1026
CTG CTA GTA GAC AGT ATA CTT CCT GGG TCT TCG TAT GAG GTT CAG GTG AGG GGC
--- --- --- --- --- --- --- --- --- --- --- --- --- --- --- --- --- ---
 L   L   V   D   S   I   L   P   G   S   S   Y   E   V   Q   V   R   G 1035        1044        1053        1062        1071        1080
AAG AGA CTG GAT GGC CCA GGA ATC TGG AGT GAC TGG AGT ACT CCT CGT GTC TTT
--- --- --- --- --- --- --- --- --- --- --- --- --- --- --- --- --- ---
 K   R   L   D   G   P   G   I   W   S   D   W   S   T   P   R   V   F 1089        1098        1107        1116        1125        1134
ACC ACA CAA GAT GTC ATA TAC TTT CCA CCT AAA ATT CTG ACA AGT GTT GGG TCT
--- --- --- --- --- --- --- --- --- --- --- --- --- --- --- --- --- ---
 T   T   Q   D   V   I   Y   F   P   P   K   I   L   T   S   V   G   S 1143        1152        1161        1170        1179        1188
AAT GTT TCT TTT CAC TGC ATC TAT AAG AAG GAA AAC AAG ATT GTT CCC TCA AAA
--- --- --- --- --- --- --- --- --- --- --- --- --- --- --- --- --- ---
 N   V   S   F   H   C   I   Y   K   K   E   N   K   I   V   P   S   K 1197        1206        1215        1224        1233        1242
GAG ATT GTT TGG TGG ATG AAT TTA GCT GAG AAA ATT CCT CAA AGC CAG TAT GAT
--- --- --- --- --- --- --- --- --- --- --- --- --- --- --- --- --- ---
 E   I   V   W   W   M   N   L   A   E   K   I   P   Q   S   Q   Y   D 1251        1260        1269        1278        1287        1296
GTT GTG AGT GAT CAT GTT AGC AAA GTT ACT TTT TTC AAT CTG AAT GAA ACC AAA
--- --- --- --- --- --- --- --- --- --- --- --- --- --- --- --- --- ---
 V   V   S   D   H   V   S   K   V   T   F   F   N   L   N   E   T   K
```

FIG.1C

```
      1305         1314          1323          1332         1341          1350
CCT CGA GGA AAG TTT ACC TAT GAT GCA GTG TAC TGC TGC AAT GAA CAT GAA TGC
 P   R   G   K   F   T   Y   D   A   V   Y   C   C   N   E   H   E   C 1359         1368          1377          1386         1395          1404
CAT CAT CGC TAT GCT GAA TTA TAT GTG ATT GAT GTC AAT ATC AAT ATC TCA TGT
 H   H   R   Y   A   E   L   Y   V   I   D   V   N   I   N   I   S   C 1413         1422          1431          1440         1449          1458
GAA ACT GAT GGG TAC TTA ACT AAA ATG ACT TGC AGA TGG TCA ACC AGT ACA ATC
 E   T   D   G   Y   L   T   K   M   T   C   R   W   S   T   S   T   I 1467         1476          1485          1494         1503          1512
CAG TCA CTT GCG GAA AGC ACT TTG CAA TTG AGG TAT CAT AGG AGC AGC CTT TAC
 Q   S   L   A   E   S   T   L   Q   L   R   Y   H   R   S   S   L   Y 1521         1530          1539          1548         1157          1566
TGT TCT GAT ATT CCA TCT ATT CAT CCC ATA TCT GAG CCC AAA GAT TGC TAT TTG
 C   S   D   I   P   S   I   H   P   I   S   E   P   K   D   C   Y   L 1575         1584          1593          1602         1611          1620
CAG AGT GAT GGT TTT TAT GAA TGC ATT TTC CAG CCA ATC TTC CTA TTA TCT GGC
 Q   S   D   G   F   Y   E   C   I   F   Q   P   I   F   L   L   S   G 1629         1638          1647          1656         1665          1674
TAC ACA ATG TGG ATT AGG ATC AAT CAC TCT CTA GGT TCA CTT GAC TCT CCA CCA
 Y   T   M   W   I   R   I   N   H   S   L   G   S   L   D   S   P   P 1683         1692          1701          1710         1719          1728
ACA TGT GTC CTT CCT GAT TCT GTG GTG AAG CCA CTG CCT CCA TCC AGT GTG AAA
 T   C   V   L   P   D   S   V   V   K   P   L   P   P   S   S   V   K
```

FIG.1D

```
      1737        1746        1755        1764        1773        1782
GCA GAA ATT ACT ATA AAC ATT GGA TTA TTG AAA ATA TCT TGG GAA AAG CCA GTC
--- --- --- --- --- --- --- --- --- --- --- --- --- --- --- --- --- ---
 A   E   I   T   I   N   I   G   L   L   K   I   S   W   E   K   P   V 1791        1800        1809        1818        1827        1836
TTT CCA GAG AAT AAC CTT CAA TTC CAG ATT CGC TAT GGT TTA AGT GGA AAA GAA
--- --- --- --- --- --- --- --- --- --- --- --- --- --- --- --- --- ---
 F   P   E   N   N   L   Q   F   Q   I   R   Y   G   L   S   G   K   E 1845        1854        1863        1872        1881        1890
GTA CAA TGG AAG ATG TAT GAG GTT TAT GAT GCA AAA TCA AAA TCT GTC AGT CTC
--- --- --- --- --- --- --- --- --- --- --- --- --- --- --- --- --- ---
 V   Q   W   K   M   Y   E   V   Y   D   A   K   S   K   S   V   S   L 1899        1908        1917        1926        1935        1944
CCA GTT CCA GAC TTG TGT GCA GTC TAT GCT GTT CAG GTG CGC TGT AAG AGG CTA
--- --- --- --- --- --- --- --- --- --- --- --- --- --- --- --- --- ---
 P   V   P   D   L   C   A   V   Y   A   V   Q   V   R   C   K   R   L 1953        1962        1971        1980        1989        1998
GAT GGA CTG GGA TAT TGG AGT AAT TGG AGC AAT CCA GCC TAC ACA GTT GTC ATG
--- --- --- --- --- --- --- --- --- --- --- --- --- --- --- --- --- ---
 D   G   L   G   Y   W   S   N   W   S   N   P   A   Y   T   V   V   M 2007        2016        2025        2034        2043        2052
GAT ATA AAA GTT CCT ATG AGA GGA CCT GAA TTT TGG AGA ATA ATT AAT GGA GAT
--- --- --- --- --- --- --- --- --- --- --- --- --- --- --- --- --- ---
 D   I   K   V   P   M   R   G   P   E   F   W   R   I   I   N   G   D 2061        2070        2079        2088        2097        2106
ACT ATG AAA AAG GAG AAA AAT GTC ACT TTA CTT TGG AAG CCC CTG ATG AAA AAT
--- --- --- --- --- --- --- --- --- --- --- --- --- --- --- --- --- ---
 T   M   K   K   E   K   N   V   T   L   L   W   K   P   L   M   K   N 2115        2124        2133        2142        2151        2160
GAC TCA TTG TGC AGT GTT CAG AGA TAT GTG ATA AAC CAT CAT ACT TCC TGC AAT
--- --- --- --- --- --- --- --- --- --- --- --- --- --- --- --- --- ---
 D   S   L   C   S   V   Q   R   Y   V   I   N   H   H   T   S   C   N
```

FIG.1E

```
      2169          2178          2187          2196          2205          2214
GGA ACA TGG TCA GAA GAT GTG GGA AAT CAC ACG AAA TTC ACT TTC CTG TGG ACA
--- --- --- --- --- --- --- --- --- --- --- --- --- --- --- --- --- ---
 G   T   W   S   E   D   V   G   N   H   T   K   F   T   F   L   W   T 2223          2232          2241          2250          2259          2268
GAG CAA GCA CAT ACT GTT ACG GTT CTG GCC ATC AAT TCA ATT GGT GCT TCT GTT
--- --- --- --- --- --- --- --- --- --- --- --- --- --- --- --- --- ---
 E   Q   A   H   T   V   T   V   L   A   I   N   S   I   G   A   S   V 2277          2286          2295          2304          2313          2322
GCA AAT TTT AAT TTA ACC TTT TCA TGG CCT ATG AGC AAA GTA AAT ATC GTG CAG
--- --- --- --- --- --- --- --- --- --- --- --- --- --- --- --- --- ---
 A   N   F   N   L   T   F   S   W   P   M   S   K   V   N   I   V   Q 2331          2340          2349          2358          2367          2376
TCA CTC AGT GCT TAT CCT TTA AAC AGC AGT TGT GTG ATT GTT TCC TGG ATA CTA
--- --- --- --- --- --- --- --- --- --- --- --- --- --- --- --- --- ---
 S   L   S   A   Y   P   L   N   S   S   C   V   I   V   S   W   I   L 2385          2394          2403          2412          2421          2430
TCA CCC AGT GAT TAC AAG CTA ATG TAT TTT ATT ATT GAG TGG AAA AAT CTT AAT
--- --- --- --- --- --- --- --- --- --- --- --- --- --- --- --- --- ---
 S   P   S   D   Y   K   L   M   Y   F   I   I   E   W   K   N   L   N 2439          2448          2457          2466          2475          2484
GAA GAT GGT GAA ATA AAA TGG CTT AGA ATC TCT TCA TCT GTT AAG AAG TAT ATA
--- --- --- --- --- --- --- --- --- --- --- --- --- --- --- --- --- ---
 E   D   G   E   I   K   W   L   R   I   S   S   S   V   K   K   Y   Y 2493          2502          2511          2520          2529          2538
ATC CAT GAT CAT TTT ATC CCC ATT GAG AAG TAC CAG TTC AGT CTT TAC CCA ATA
--- --- --- --- --- --- --- --- --- --- --- --- --- --- --- --- --- ---
 I   H   D   H   F   I   P   I   E   K   Y   Q   F   S   L   Y   P   I 2547          2556          2565          2574          2583          2592
TTT ATG GAA GGA GTG GGA AAA CCA AAG ATA ATT AAT AGT TTC ACT CAA GAT GAT
--- --- --- --- --- --- --- --- --- --- --- --- --- --- --- --- --- ---
 F   M   E   G   V   G   K   P   K   I   I   N   S   F   T   Q   D   D
```

FIG. 1F

```
     2601           2610            2619           2628           2637           2646
ATT GAA AAA CAC CAG AGT GAT GCA GGT TTA TAT GTA ATT GTG CCA GTA ATT ATT
--- --- --- --- --- --- --- --- --- --- --- --- --- --- --- --- --- ---
 I   E   K   H   Q   S   D   A   G   L   Y   V   I   V   P   V   I   I 2655           2664            2673           2682           2691           2700
TCC TCT TCC ATC TTA TTG CTT GGA ACA TTA TTA ATA TCA CAC CAA AGA ATG AAA
--- --- --- --- --- --- --- --- --- --- --- --- --- --- --- --- --- ---
 S   S   S   I   L   L   L   G   T   L   L   I   S   H   Q   R   M   K 2709           2718            2727           2736           2745           2754
AAG CTA TTT TGG GAA GAT GTT CCG AAC CCC AAG AAT TGT TCC TGG GCA CAA GGA
--- --- --- --- --- --- --- --- --- --- --- --- --- --- --- --- --- ---
 K   L   F   W   E   D   V   P   N   P   K   N   C   S   W   A   Q   G 2763           2772            2781           2790           2799           2808
CTT AAT TTT CAG AAG AGA ACG GAC ATT CTT TGA AGT CTA ATC ATG ATC ACT ACA
--- --- --- --- --- --- --- --- --- --- --- --- --- --- --- --- --- ---
 L   N   F   Q   K   R   T   D   I   L   *   S   L   I   M   I   T   T 2817           2826            2835           2844           2853           2862
GAT GAA CCC AAT GTG CCA ACT TCC CAA CAG TCT ATA GAG TAT TAG AAG ATT TTT
--- --- --- --- --- --- --- --- --- --- --- --- --- --- --- --- --- ---
 D   E   P   N   V   P   T   S   Q   Q   S   I   E   Y   *   K   I   F

2871
ACA TTC TGA AGA AGG 3'
--- --- --- --- ---
 T   F   *   R   R
```

FIG.1G

METHODS FOR IDENTIFYING COMPOUNDS CAPABLE OF SUPPLEMENTING THE BIOLOGICAL ACTIVITY OF LEPTIN

This application is a division of application Ser. No. 08/588,189, filed on Jan. 18, 1996, currently U.S. Pat. No. 6,451,523, which is a continuation-in-part of U.S. patent application Ser. No. 08/355,888 filed Dec. 14, 1994, currently U.S. Pat. No. 5,763,211, issued Jun. 9, 1998, which is a continuation-in-part of U.S. patent application Ser. No.08/306,231 filed Sep. 14, 1994, currently U.S. Pat. No. 5,643,748, issued Jul. 1, 1997, each of which is incorporated herein in its entirety.

1. INTRODUCTION

The present invention relates to a variant form of the receptor for the obese gene product. In particular, the invention relates to methods of detecting this receptor variant in cells and tissues of obese individuals. In addition, it relates to methods of inhibiting or down-regulating expression of this variant in cells to augment their responsiveness to weight regulation by leptin as well as methods of using compounds to directly activate signal transduction pathways associated with this ligand-receptor system.

2. BACKGROUND OF THE INVENTION

Obesity is not only a nutritional disorder in Western societies, it is also a serious health concern because of its association with adult-onset diabetes, hypertension, and heart disease (Grundy, 1990, *Disease-a-Month* 36:645–696). While there was evidence to suggest that body weight was physiologically regulated, the molecular mechanism has remained elusive. However, animal studies have produced several mouse strains that contain single-gene mutations, resulting in an obese phenotype. One such recessive mutation is manifested in the ob/ob mice, and it is referred to as the obese (ob) mutation.

Zhang et al. (1994, *Nature* 372:425–432) describe the cloning and sequencing of the mouse ob gene and its human homolog. When an isolated gene fragment was used as a probe, it was shown to hybridize with RNA only in white adipose tissue by northern blot analysis, but no expression was detected in any other tissue. In addition, the coding sequence of the ob gene hybridized to all vertebrate genomic DNAs tested, indicating a high level of conservation of this molecule among vertebrates. The deduced amino acid sequences are 84% identical between human and mouse, and both molecules contain features of secreted proteins.

In an effort to understand the physiologic function of the ob gene, several independent research groups produced recombinant ob gene product in bacteria for in vivo testing (Pelleymounter et al., 1995, *Science* 269:540–543; Halaas et al., 1995, *Science* 269:543–546; Campfield et al., 1995, *Science* 269:546–549). When the Ob protein (also known as leptin) was injected into grossly obese mice, which possessed two mutant copies of the ob gene, the mice exhibited a reduced appetite and began to lose weight. In addition, these studies described a dual action of leptin in both reducing the animals' food intake and in increasing their energy expenditure. Similarly, when normal mice received leptin, they also ate less than the untreated controls. More importantly, Campfield et al. (1995, *Science* 269:546–549) injected leptin directly into lateral ventricle, and observed a reduction in the animals' food intake, suggesting that leptin acts on central neuronal networks to regulate feeding behavior and energy balance. Thus, this result provides evidence that the leptin receptor (also known as OB-R) is expressed by cells in the brain.

Recently, a leptin fusion protein was generated and used to screen for OB-R in a cDNA expression library prepared from mouse choroid plexus, a tissue that lines brain cavities termed ventricles (Tartalia, 1995, *Cell* 83:1263–1271). This approach led to the cloning of one form of the OB-R coding sequence, which reveals a single membrane-spanning receptor, sharing structural similarities with several Class I cytokine receptors, such as the gp130 signal-transducing component of the interleukin-6 receptor (Taga et al., 1989, *Cell* 58:573–581), the granulocyte-colony stimulating factor receptor (Fukunaga et al., 1990, *Cell* 61:341–350), and the leukemia inhibitory factor receptor (Gearing et al., 1991, *EMBO J.* 10:2839–2848). Northern blot analysis and reverse transcription-polymerase chain reaction (RT-PCR) demonstrate that OB-R mRNA is expressed in several tissues, including lung, kidney, total brain, choroid plexus and hypothalamus.

The reported mouse OB-R protein contains a relatively short intracellular cytoplasmic domain as compared with other Class I cytokine receptors. Subsequently, when cDNA encoding its human homolog was isolated from a human infant brain library, the predicted human protein sequence contains a much longer intracellular domain. In view of this finding, it was speculated that different forms of the receptor might exist (Barinaga, 1996, *Science* 271:29). However, prior to the present invention, there was no report on the identification of any variant forms of the OB-R in humans or how such molecules, if they exist, would relate to obesity.

Additionally, several studies have shown that ob gene expression is actually increased in obese humans (Considine et al., 1995, *J. Clin. Invest.* 95:2986–2988; Lonnquist et al., 1995, *Nature Med.* 1:950; Hamilton et al., 1995, *Nature Med.* 1:953). Moreover, the mutations in the mouse Ob gene were not detected in human mRNA. Therefore, taken collectively, these studies imply that decreased leptin levels are not the primary cause of obesity, and argue for the presence of a less responsive receptor in obese individuals. There remains a need to isolate such an OB-R variant for the design of therapeutics to augment weight regulation by leptin.

3. SUMMARY OF THE INVENTION

The present invention relates to a variant form of the human OB-R. In particular, it relates to the detection of this receptor variant in cells of obese individuals, and methods for treating obesity by targeting this variant.

The invention is based, in part, upon the Applicants' discovery of human cDNA clones encoding a variant form of the OB-R. This receptor differs structurally from a reported OB-R with only three amino acid substitutions in the extracellular domain, but extensive diversity is observed in their intracellular cytoplasmic domains at the 3' end. The cytoplasmic domain of the variant of the invention is both shorter and distinct in nucleotide sequence from the corresponding domain of the published form of OB-R. Therefore, a wide variety of uses are encompassed by the present invention, including but not limited to, the detection of the receptor variant in cells of obese individuals, methods to inhibit and/or down-regulate the expression of this receptor variant, gene therapy to replace the receptor variant in homozygous individuals, and direct activation of downstream signal transduction pathways in cells expressing the receptor variant for weight regulation.

4. BRIEF DESCRIPTION OF THE DRAWINGS

FIGS. 1A–1G. Nucleotide sequence (SEQ ID NO:1) and deduced amino acid sequence (SEQ ID NOs:2–5) of the human OB-R variant. The amino acid sequence diverges from the human OB-R reported by Tartaglia et al. (1995, Cell 83:1263–1271) at nucleotide residue #349, #422, #764 and from residue #2770 and beyond.

5. DETAILED DESCRIPTION OF THE INVENTION

5.1. The OB-R Variant

The present invention relates to nucleic acid and amino acid sequences of an OB-R variant in the Class I cytokine receptor family. In a specific embodiment by way of example in Section 6, infra, this variant was cloned and characterized. Amino acid sequence comparison of this OB-R variant with a published human OB-R sequence (Tartaglia et al., 1995, Cell 83:1263–1271) reveals three amino acid differences in their extracellular domain and extensive diversity in their intracellular cytoplasmic domains. More specifically, FIGS. 1A–1E shows that in the variant, nucleotide residues #349–351 encode alanine, nucleotide residues #421–423 encode arginine and nucleotide residues #763–765 encode arginine. Additionally, the variant diverges both in length and sequence composition from the published human OB-R sequence from nucleotide residue #2770 and beyond.

In order to clone additional variant forms of the molecule, labeled DNA probes made from nucleic acid fragments corresponding to any portion of the cDNA disclosed herein may be used to screen a cDNA library prepared from human fetal liver, human lung, human kidney, human choroid plexus and human hypothalamus. More specifically, oligonucleotides corresponding to either the 5' or 3' terminus of the cDNA sequence may be used to obtain longer nucleotide sequences. Briefly, the library may be plated out to yield a maximum of 30,000 pfu for each 150 mm plate. Approximately 40 plates may be screened. The plates are incubated at 37° C. until the plaques reach a diameter of 0.25 mm or are just beginning to make contact with one another (3–8 hours). Nylon filters are placed onto the soft top agarose and after 60 seconds, the filters are peeled off and floated on a DNA denaturing solution consisting of 0.4N sodium hydroxide. The filters are then immersed in neutralizing solution consisting of 1M Tris HCL, pH 7.5, before being allowed to air dry. The filters are prehybridized in casein hybridization buffer containing 10% dextran sulfate, 0.5M NaCl, 50 mM Tris HCL, pH 7.5, 0.1% sodium pyrosphosphate, 1% casein, 1% SDS, and denatured salmon sperm DNA at 0.5 mg/ml for 6 hours at 60° C. The radiolabelled probe is then denatured by heating to 95° C. for 2 minutes and then added to the prehybridization solution containing the filters. The filters are hybridized at 60° C. for 16 hours. The filters are then washed in 1× wash mix (10× wash mix contains 3M NaCl, 0.6M Tris base, and 0.02M EDTA) twice for 5 minutes each at room temperature, then in 1× wash mix containing 1% SDS at 60° C. for 30 minutes, and finally in 0.3× wash mix containing 0.1% SDS at 60° C. for 30 minutes. The filters are then air dried and exposed to x-ray film for autoradiography. After developing, the film is aligned with the filters to select a positive plaque. If a single, isolated positive plaque cannot be obtained, the agar plug containing the plaques will be removed and placed in lambda dilution buffer containing 0.1M NaCl, 0.01M magnesium sulfate, 0.035M Tris HCl, pH 7.5, 0.01% gelatin. The phage may then be replated and rescreened to obtain single, well isolated positive plaques. Positive plaques may be isolated and the cDNA clones sequenced using primers based on the known cDNA sequence. This step may be repeated until a full length cDNA is obtained.

One method for identifying all 3' isoforms is to PCR amplify the 3' ends of the variant cDNA from a variety of tissues including but not limiting to, choroid plexus, hypothalamus, fetal liver, bone marrow, ovary, or prostate. To obtain the 3' end of the cDNA, an oligo-dT primer is used to synthesize the cDNA first strand. OB-R specific primers from the conserved region of the gene (e.g. up stream of nucleotide 2770) and oligo-dT are then used to amplify the 3' end. The PCR fragments are cloned and sequenced by standard techniques. Once obtained, these sequences may be translated into amino acid sequence and examined for certain landmarks such as continuous open reading frame, regulatory regions that associate with tyrosine kinase activation, and finally overall structural similarity to known OB-R variants.

5.2. Expression of the OB-R Variant

In accordance with the invention, the OB-R variant polynucleotide sequence which encodes a protein, peptide fragments, fusion proteins or functional equivalents thereof, may be used to generate recombinant DNA molecules that direct the expression of the protein, peptide fragments, fusion proteins or a functional equivalent thereof, in appropriate host cells. Such polynucleotide sequences, as well as other polynucleotides which selectively hybridize to at least a part of such polynucleotides or their complements, may also be used in nucleic acid hybridization assays, Southern and Northern blot analyses, etc.

Due to the inherent degeneracy of the genetic code, other DNA sequences which encode substantially the same or a functionally equivalent amino acid sequence, may be used in the practice of the invention for the expression of the OB-R variant. Such DNA sequences include those which are capable of hybridizing to the OB-R variant sequence under stringent conditions, particularly at its 3' end. The phrase "stringent conditions" as used herein refers to those hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M Sodium pyrophosphate, 5× Denhardt's solution, sonicated salmon sperm DNA (50 g/ml), 0.1% SDS, and 10% dextran sulfate at 42° C., with washes at 42° C. in 0.2×SSC and 0.1% SDS.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within the OB-R variant sequence, which result in a silent change thus producing a functionally equivalent protein. Such amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, serine, threonine, tyrosine; and amino acids with nonpolar head groups include alanine, valine, isoleucine, leucine, phenylalanine, proline, methionine, tryptophan.

The DNA sequence of the invention may be engineered in order to alter the OB-R variant coding sequence for a variety of ends, including but not limited to, alterations which modify processing and expression of the gene product. For example, mutations may be introduced using techniques which are well known in the art, e.g., site-directed mutagenesis, to insert new restriction sites, to alter glycosylation patterns, phosphorylation, etc. In addition, the intracellular domain may also be altered and replaced by a different domain, such as the OB-R intracellular domain by Tartaglia et al.

In another embodiment of the invention, the OB-R variant sequence may be ligated to a heterologous sequence to encode a fusion protein. For example, for screening of peptide libraries for inhibitors or stimulators of receptor activity, it may be useful to encode a chimeric protein expressing a heterologous epitope that is recognized by a commercially available antibody. A fusion protein may also be engineered to contain a cleavage site located between the OB-R variant sequence and the heterologous protein sequence, so that the variant may be cleaved away from the heterologous moiety.

In an alternate embodiment of the invention, the coding sequence of the OB-R variant could be synthesized in whole or in part, using chemical methods well known in the art. (See, for example, Caruthers et al., 1980, *Nuc. Acids Res. Symp. Ser.* 7:215–233; Crea and Horn, 180, *Nuc. Acids Res.* 9(10):2331; Matteucci and Caruthers, 1980, *Tetrahedron Letters* 21:719; and Chow and Kempe, 1981, *Nuc. Acids Res.* 9(12):2807–2817) . Alternatively, the protein itself could be produced using chemical methods to synthesize OB-R variant amino acid sequence in whole or in part. For example, peptides can be synthesized by solid phase techniques, cleaved from the resin, and purified by preparative high performance liquid chromatography. (e.g., see Creighton, 1983, *Proteins Structures And Molecular Principles,* W.H. Freeman and Co., N.Y. pp. 50–60). The composition of the synthetic peptides may be confirmed by amino acid analysis or sequencing (e.g., the Edman degradation procedure; see Creighton, 1983, *Proteins, Structures and Molecular Principles,* W.H. Freeman and Co., N.Y., pp. 34–49).

In order to express the OB-R variant in host cells, the nucleotide sequence coding for the variant, or a functional equivalent, is inserted into an appropriate expression vector, i.e., a vector which contains the necessary elements for the transcription and translation of the inserted coding sequence. The expressed gene products as well as host cells or cell lines transfected or transformed with recombinant OB-R variant expression vectors can be used for a variety of purposes. For example, host cells expressing the OB-R variant may be used to verify the ability of this molecule to bind leptin in a binding assay with radiolabeled, enzyme-conjugated or fluorescent dye-conjugated leptin. At the same time, the ability of the molecule to transduce an activation signal in host cells upon binding to leptin may be tested by assaying proliferation or phosphorylation pattern of kinases in the cells. In addition, genetically-engineered host cells can be used to screen for and select agonist and antagonist compounds, including any inhibitors that would interfere with binding of leptin to the extracellular domain of the OB-R variant. In that connection, such host cells may be used to screen for and select small molecules that can supplement the incomplete signal transduced by the OB-R variant following leptin binding. Other uses, include, but are not limited to generating antibodies (i.e., monoclonal or polyclonal) that competitively inhibit activity of an OB-R variant, neutralize its activity, or even enhances it activity. Antibodies may be used in detecting and quantifying expression of OB-R levels in cells and tissues.

5.3. Uses of the OB-R Variant Polynucleotide

The OB-R variant polynucleotide may be used for diagnostic and/or therapeutic purposes. For diagnostic purposes, the OB-R variant polynucleotide may be used to detect gene expression or aberrant gene expression in obese individuals as well as in normal individuals to identify predisposition for obesity. Included in the scope of the invention are oligonucleotide sequences, that include antisense RNA and DNA molecules, ribozymes and triplex DNA, that function to inhibit translation of OB-R variant.

5.3.1. Diagnostic Uses of OB-R Variant Polynucleotide

The OB-R variant polynucleotide may have a number of uses for the diagnosis of the possible causes underlying obesity, resulting from expression of the receptor variant. For example, the OB-R variant cytoplasmic domain DNA sequence may be used in hybridization assays of biopsies or autopsies to diagnose OB-R variant expression; e.g., Southern or Northern analysis, including in situ hybridization assays as well as PCR. Such techniques are well known in the art, and are in fact the basis of many commercially available diagnostic kits. For PCR detection, primers may be designed from a conserved region of the coding sequence and within the 3' region of OB-R variant. The tissues suitable for such analysis include but are not limited to, hypothalamus, choroid plexus, adipose tissues, lung, prostate, ovary, small intestine, bone marrow and peripheral blood mononuclear cells.

5.3.2. Therapeutic Uses of the OB-R Variant Polynucleotide

The OB-R variant polynucleotide may be useful in the treatment of various abnormal obese conditions. By introducing gene sequences into cells, gene therapy can be used to treat conditions in which the cells do not respond to leptin normally due to expression of the OB-R variant. In some instances, the polynucleotide encoding a functional OB-R is intended to replace or act in the place of the functionally deficient OB-R variant gene. Alternatively, abnormal conditions characterized by expression of two copies of the OB-R variant can be treated using the gene therapy techniques described below.

Non-responsiveness to normal levels of leptin is an important cause of obesity. This may result from a functionally defective receptor that does not transduce competent signals upon ligand binding. Recombinant gene therapy vectors, such as viral vectors, may be engineered to express signalling competent forms of OB-R which may be used to augment the non-responsiveness of the naturally occurring OB-R variant. A signalling competent form may be, for example, a protein with the same extracellular domain and transmembrane region, but containing all or part of its normal signal transduction domain, such as that described by Tartaglia et al. (1995, *Cell* 83:1263–1271). Thus recombinant gene therapy vectors may be used therapeutically for treatment of obesity resulting from expression or activity of the OB-R variant. Accordingly, the invention provides a method of augmenting signal transduction by an endogenous OB-R variant in a cell comprising delivering a DNA molecule encoding a signalling competent form of the OB-R to the cell so that the signalling competent protein is produced in the cell and competes with the endogenous defective OB-R variant for access to molecules in the signalling pathway which does not activate or are not activated by the endogenous natural defective receptor. Additionally, since dimerization of a functional receptor with a defective variant may occur in cells of heterozygous individuals, small molecules may be used to inhibit such pairing, thereby increasing the number of functional dimeric receptors for proper signalling in response to leptin.

In contrast, overexpression of either leptin or a competent OB-R may result in a clinical anorexic-like syndrome due to a loss of appetite or hypermetabolic activity. In such cases, the OB-R variant of the invention may be introduced into cells with functional receptors to cause a decrease in the number of functional receptors or to compete with such receptors for leptin binding.

Expression vectors derived from viruses such as retroviruses, vaccinia virus, adeno-associated virus, herpes viruses, or bovine papilloma virus, may be used for delivery of recombinant functional OB-R into the targeted cell population. Methods which are well known to those skilled in the art can be used to construct recombinant viral vectors containing an OB-R polynucleotide sequence. See, for example, the techniques described in Sambrook et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y. Alternatively, recombinant OB-R molecules can be reconstituted into liposomes for delivery to target cells.

Oligonucleotide sequences including anti-sense RNA and DNA molecules and ribozymes that function to inhibit the translation of the OB-R variant mRNA are within the scope of the invention. Anti-sense RNA and DNA molecules act to directly block the translation of mRNA by binding to targeted mRNA and preventing protein translation. In regard to antisense DNA, oligodeoxyribonucleotides derived from the OB-R variant nucleotide sequence at nucleotide #2771 and beyond, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Within the scope of the invention are engineered hammerhead motif ribozyme molecules that specifically and efficiently catalyze endonucleolytic cleavage of OB-R variant RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Oligodeoxyribonucleotides can form sequence-specific triple helices by hydrogen bonding to specific complementary sequences in duplexed DNA. Interest in triple helices has focused on the potential biological and therapeutic applications of these structures. Formation of specific triple helices may selectively inhibit the replication and/or gene expression of targeted genes by prohibiting the specific binding of functional trans-acting factors.

Oligonucleotides to be used in triplex helix formation should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Oligonucleotide sequences may be pyrimidine-based, which will result in TAT and CGC triplets across the three associated strands of the resulting triple helix. The pyrimidine-rich oligonucleotides provide base complementarity to a purine-rich region of a single strand of the duplex in a parallel orientation to that strand. In addition, oligonucleotides may be chosen that are purine-rich, for example, containing a stretch of G residues. These oligonucleotides will form a triple helix with a DNA duplex that is rich in GC pairs, in which the majority of the purine residues are located on a single strand of the targeted duplex, resulting in GGC triplets across the three strands in the triplex. Alternatively, the potential sequences that can be targeted for triple helix formation may be increased by creating a so called "switchback" oligonucleotide. Switchback oligonucleotides are synthesized in an alternating 5'-3', 3'-5' manner, such that they base pair with first one strand of a duplex and then the other, eliminating the necessity for a sizeable stretch of either purines or pyrimidines to be present on one strand of a duplex.

Both anti-sense RNA and DNA molecules and ribozymes of the invention may be prepared by any method known in the art for the synthesis of RNA molecules. These include techniques for chemically synthesizing oligodeoxyribonucleotides well known in the art such as solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleo-tide backbone.

5.4. Activation of Tyrosine Kinase Pathways in Obesity

Many known class I cytokine receptors initiate cell signaling via Janus kinases (JAKs) (Ihle, 1995, *Nature* 377:591–594; Heldin, 1995, *Cell* 80:213–223; Kishimoto et al, 1994, *Cell* 76:253–62; Ziemiecki et al, 1994, *Trends Cell. Biol.* 4:207–212). JAK1-3 have been shown to bind to conserved sequences termed box1 and box2 (Fukunaga et al., 1991, *EMBO J.* 10:2855–65; Murakami, 1991, *Proc. Natl. Acad. Sci. USA* 88:11349–53). Ligand binding induces a homo- or hetero-dimerization of receptor chains which activates, by phosphorylation, the JAKs. The activated JAKs, in turn, phosphorylate members of the STAT family (Heldin, 1995, *Cell* 80:213–223; Kishimoto et al., *Blood* 86:1243–54; Darnell et al., 1994, *Science* 264:1415–21; Zhong et al, 1994, *Proc. Natl. Acad. Sci. USA* 91:4806–10; Hou et al., 1994, *Science* 265:1701–6). These phosphorylated STATs ultimately translocate to the nucleus, form transcription complexes, and regulate gene expression. Both box1 and box2 are required for complete signaling in certain systems. (Fukunaga et al., 1991, EMBO J. 10:2855–65; Murakami, 1991, Proc. Natl. Acad. Sci. USA 88:11349–53). The OB-R variant disclosed herein has a typical box1 (from nucleotide #2707–2730) that contains the critical xWxxx-PxP amino acid sequence, but it does not contain an obvious box2 nor further downstream sequences that are important for normal receptor activation. Therefore, it is possible to use compounds that activate JAKs to directly activate these pathways for weight regulation without triggering the OB-R.

6. EXAMPLE

Molecular Cloning of an OB-R Variant

A number of cDNA clones were isolated from a human fetal liver cDNA library (Clontech, Palo Alto, Calif.), and the DNA sequences of several of these clones were determined. These clones (designated as Hu-B1.219 #4, #33, #34, #1, #3, #57, #62) contained overlapping sequences, which were then compiled into a contiguous nucleotide sequence (SEQ ID NO:1) (FIGS. 1A–1G). When the deduced amino acid sequence (SEQ ID NOs:2–5) of one such sequence was compared with the sequence of a recently published human OB-R, they were shown to be nearly identical in the extracellular domains with the exception of three amino acids, whereas there existed extensive diversity in their intracellular cytoplasmic domains at the 3' end. The predicted protein sequence contains two FN III domains, each containing a "WS box", which are characteristic of genes of the Class I cytokine receptor family. Therefore, the cDNA disclosed herein encodes an OB-R variant.

When various human tissue RNA were probed with a fragment of this OB-R variant by Northern blot analysis, expression of this molecule was detected in heart, placenta, lung, liver, muscle, pancreas, prostate, ovary, small intestine and brain.

Based on the sequence presented in FIGS. 1A–1G (SEQ ID NO:1), the translation initiation site appears at position #97. The sequence encodes an open reading frame up to and including nucleotide #2784. It is believed that the sequence between nucleotides #2629 and #2682 encodes a transmembrane domain. The complete sequence encodes a protein of 896 amino acids.

The sequence of the OB-R variant is identical to the sequence of human OB-R reported by Tartaglia (1995, *Cell* 83:1263–1271) in the transmembrane region and a portion of the intracellular domain up to and including nucleotide #2769, then they diverge at nucleotide #2770 and beyond. In addition, the product of this cDNA is substantially shorter in its intracellular domain than the published human OB-R. These two forms of OB-R may derive from a common precursor mRNA by an alternative splicing mechanism. The sequence in this region is consistent with well known splice junctions.

7. DEPOSIT OF MICROORGANISMS

The following organisms were deposited with the American Type Culture Collection (ATCC), 12301 Parklawn Drive, Rockville, Md. 20852.

| Strain Designation | Accession No. |
| --- | --- |
| HuB1.219, #1 | 75885 |
| HuB1.219, #4 | 75886 |
| HuB1.219, #33 | 75888 |
| HuB1.219, #34 | 75889 |
| HuB1.219, #3 | 75970 |
| HuB1.219, #57 | 75972 |
| HuB1.219, #62 | 75974 |

The present invention is not to be limited in scope by the exemplified embodiments, which are intended as illustrations of individual aspects of the invention. Indeed, various modifications for the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method for identifying a compound capable of supplementing biological activity of leptin on cells expressing a leptin receptor variant, comprising:
   (a) incubating host cells with leptin to form a population of leptin-treated cells, wherein the host cells express a leptin-binding leptin receptor variant encoded by a polynucleotide selected from the group consisting of:
      (i) the polynucleotide sequence of SEQ ID NO:1;
      ii) a polynucleotide that hybridizes to a nucleic acid comprising the complement of the polynucleotide of (i) under stringent conditions; and
      iii) a portion of the polynucleotide of (i) that hybridizes to a nucleic acid comprising the complement of the polynucleotide of (i) under stringent conditions;
   wherein the leptin-binding leptin receptor variant does not produce competent signals upon leptin binding;
   wherein the stringent conditions recited in (ii), and (iii) comprise either:
      i) washing at 50° C. with 0.015 M NaCl, 0.0015 M sodium citrate and 0.1% SDS; or
      ii) washing at 42° C. in 0.2%×SSC and 0.1% SDS;
   (b) incubating control host cells that do not express a leptin receptor with leptin;
   (c) incubating a portion of the cells of step (a) with a test compound;
   (d) incubating a portion of the cells of step (b) with a test compound; and
   (e) comparing activation signal in the leptin-treated cells of steps (a), (b), and (d) with that the activation signal of the cells of step (c),
   wherein a compound capable of supplementing a biological activity of leptin is identified if a higher activation signal is obtained for the cells of step (c) compared to the cells of steps (a), (b), and (d); thereby determining whether the compound supplements activation of the leptin receptor variant by leptin.

2. The method of claim 1, wherein the activation signal is detected by assaying for cell proliferation or a phosphorylation pattern of kinases in the leptin-treated cells.

3. The method of claim 2, wherein the kinases are Janus kinases.

4. The method of claim 2, wherein the host cells are genetically engineered to expresses the leptin receptor variant.

5. The method of claim 2, wherein the test compound is an antibody.

6. The method of claim 2, wherein the test compound is a small molecule.

7. The method of claim 2, wherein the test compound is an agonist that enhances the binding of leptin to the leptin receptor variant.

8. The method of claim 7, wherein the binding of leptin to the leptin receptor variant is verified using radiolabeled leptin, enzyme-conjugated leptin, or fluorescent dye-conjugated leptin.

9. The method of claim 5, wherein the antibody is polyclonal or monoclonal.

10. A method for identifying a compound capable of interfering with the binding of leptin to the extracellular domain of a leptin receptor variant comprising:
    (a) incubating host cells with leptin to form a population of leptin-treated cells wherein the host cells express a leptin-binding leptin receptor variant encoded by a polynucleotide selected from the group consisting of:
       (i) the polynucleotide sequence of SEQ ID NO:1;
       (ii) a polynucleotide that hybridizes to a nucleic acid comprising the complement of the polynucleotide of (i) under stringent conditions; and
       (iii) a portion of the polynucleotide of (i) that hybridizes to a nucleic acid comprising the complement of the polynucleotide of (i) under stringent conditions;
    wherein the leptin-binding leptin receptor variant does not produce competent signals upon leptin binding;
    wherein the stringent conditions recited in (ii), and (iii) comprise either:
       (i) washing at 50° C. with 0.015 M NaCl, 0.0015 M sodium citrate and 0.1% SDS; or
       (ii) washing at 42° C in 0.2%×SSC and 0.1% SDS;
    (b) incubating a portion of the leptin-treated cells with a test compound; and
    (c) measuring the level of leptin bound to the leptin-treated cells in the presence and absence of the test compound, such that if the level of leptin bound to the leptin-treated cells in the presence of the test compound is less that the level of leptin bound to the leptin-treated cells in the absence of the test compound then a compound that interferes with the binding of leptin to a leptin receptor variant is identified.

11. The method of claim 10, wherein the binding of leptin to the leptin receptor variant is assayed using radiolabeled leptin, enzyme-conjugated leptin, or fluorescent dye-conjugated leptin.

* * * * *

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
          (A) LENGTH: 2877 base pairs
          (B) TYPE: nucleic acid
          (C) STRANDEDNESS: single
          (D) TOPOLOGY: linear (ii) MOLECULE TYPE: cDNA (ix) FEATURE:
          (A) NAME/KEY: CDS
          (B) LOCATION: 1..2871

(xi) SEQUENCE DESCRIPTION: SEQ ID NO: 1:

```
GCG CGC GCG ACG CAG GTG CCC GAG CCC CGG CCC GCG CCC ATC TCT GCC          48
Ala Arg Ala Thr Gln Val Pro Glu Pro Arg Pro Ala Pro Ile Ser Ala
 1               5                  10                  15

TTC GGT CGA GTT GGA CCC CCG GAT CAA GGT GTA CTT CTC TGA AGT AAG          96
Phe Gly Arg Val Gly Pro Pro Asp Gln Gly Val Leu Leu Xaa Ser Lys
                20                  25                  30

ATG ATT TGT CAA AAA TTC TGT GTG GTT TTG TTA CAT TGG GAA TTT ATT         144
Met Ile Cys Gln Lys Phe Cys Val Val Leu Leu His Trp Glu Phe Ile
         35                  40                  45

TAT GTG ATA ACT GCG TTT AAC TTG TCA TAT CCA ATT ACT CCT TGG AGA         192
Tyr Val Ile Thr Ala Phe Asn Leu Ser Tyr Pro Ile Thr Pro Trp Arg
     50                  55                  60

TTT AAG TTG TCT TGC ATG CCA CCA AAT TCA ACC TAT GAC TAC TTC CTT         240
Phe Lys Leu Ser Cys Met Pro Pro Asn Ser Thr Tyr Asp Tyr Phe Leu
 65                  70                  75                  80

TTG CCT GCT GGA CTC TCA AAG AAT ACT TCA AAT TCG AAT GGA CAT TAT         288
Leu Pro Ala Gly Leu Ser Lys Asn Thr Ser Asn Ser Asn Gly His Tyr
                85                  90                  95

GAG ACA GCT GTT GAA CCT AAG TTT AAT TCA AGT GGT ACT CAC TTT TCT         336
Glu Thr Ala Val Glu Pro Lys Phe Asn Ser Ser Gly Thr His Phe Ser
               100                 105                 110

AAC TTA TCC AAA GCA ACT TTC CAC TGT TGC TTT CGG AGT GAG CAA GAT         384
Asn Leu Ser Lys Ala Thr Phe His Cys Cys Phe Arg Ser Glu Gln Asp
       115                 120                 125

AGA AAC TGC TCC TTA TGT GCA GAC AAC ATT GAA GGA AGG ACA TTT GTT         432
Arg Asn Cys Ser Leu Cys Ala Asp Asn Ile Glu Gly Arg Thr Phe Val
   130                 135                 140

TCA ACA GTA AAT TCT TTA GTT TTT CAA CAA ATA GAT GCA AAC TGG AAC         480
Ser Thr Val Asn Ser Leu Val Phe Gln Gln Ile Asp Ala Asn Trp Asn
145                 150                 155                 160

ATA CAG TGC TGG CTA AAA GGA GAC TTA AAA TTA TTC ATC TGT TAT GTG         528
Ile Gln Cys Trp Leu Lys Gly Asp Leu Lys Leu Phe Ile Cys Tyr Val
               165                 170                 175

GAG TCA TTA TTT AAG AAT CTA TTC AGG AAT TAT AAC TAT AAG GTC CAT         576
Glu Ser Leu Phe Lys Asn Leu Phe Arg Asn Tyr Asn Tyr Lys Val His
           180                 185                 190

CTT TTA TAT GTT CTG CCT GAA GTG TTA GAA GAT TCA CCT CTG GTT CCC         624
Leu Leu Tyr Val Leu Pro Glu Val Leu Glu Asp Ser Pro Leu Val Pro
       195                 200                 205

CAA AAA GGC AGT TTT CAG ATG GTT CAC TGC AAT TGC AGT GTT CAT GAA         672
Gln Lys Gly Ser Phe Gln Met Val His Cys Asn Cys Ser Val His Glu
   210                 215                 220

TGT TGT GAA TGT CTT GTG CCT GTG CCA ACA GCC AAA CTC AAC GAC ACT         720
Cys Cys Glu Cys Leu Val Pro Val Pro Thr Ala Lys Leu Asn Asp Thr
225                 230                 235                 240

CTC CTT ATG TGT TTG AAA ATC ACA TCT GGT GGA GTA ATT TTC CGG TCA         768
Leu Leu Met Cys Leu Lys Ile Thr Ser Gly Gly Val Ile Phe Arg Ser
               245                 250                 255

CCT CTA ATG TCA GTT CAG CCA ATA AAT ATG GTG AAG CCT GAT CCA CCA         816
Pro Leu Met Ser Val Gln Pro Ile Asn Met Val Lys Pro Asp Pro Pro
           260                 265                 270

TTA GGT TTG CAT ATG GAA ATC ACA GAT GAT GGT AAT TTA AAG ATT TCT         864
Leu Gly Leu His Met Glu Ile Thr Asp Asp Gly Asn Leu Lys Ile Ser
       275                 280                 285

TGG TCC AGC CCA CCA TTG GTA CCA TTT CCA CTT CAA TAT CAA GTG AAA         912
Trp Ser Ser Pro Pro Leu Val Pro Phe Pro Leu Gln Tyr Gln Val Lys
   290                 295                 300

TAT TCA GAG AAT TCT ACA ACA GTT ATC AGA GAA GCT GAC AAG ATT GTC         960
Tyr Ser Glu Asn Ser Thr Thr Val Ile Arg Glu Ala Asp Lys Ile Val
```

| | | |
|---|---|---|
| TCA GCT ACA TCC CTG CTA GTA GAC AGT ATA CTT CCT GGG TCT TCG TAT<br>Ser Ala Thr Ser Leu Leu Val Asp Ser Ile Leu Pro Gly Ser Ser Tyr<br>    325                     330                     335 | | 1008 |
| GAG GTT CAG GTG AGG GGC AAG AGA CTG GAT GGC CCA GGA ATC TGG AGT<br>Glu Val Gln Val Arg Gly Lys Arg Leu Asp Gly Pro Gly Ile Trp Ser<br>            340                     345                     350 | | 1056 |
| GAC TGG AGT ACT CCT CGT GTC TTT ACC ACA CAA GAT GTC ATA TAC TTT<br>Asp Trp Ser Thr Pro Arg Val Phe Thr Thr Gln Asp Val Ile Tyr Phe<br>                355                     360                     365 | | 1104 |
| CCA CCT AAA ATT CTG ACA AGT GTT GGG TCT AAT GTT TCT TTT CAC TGC<br>Pro Pro Lys Ile Leu Thr Ser Val Gly Ser Asn Val Ser Phe His Cys<br>    370                     375                     380 | | 1152 |
| ATC TAT AAG AAG GAA AAC AAG ATT GTT CCC TCA AAA GAG ATT GTT TGG<br>Ile Tyr Lys Lys Glu Asn Lys Ile Val Pro Ser Lys Glu Ile Val Trp<br>385                     390                     395                 400 | | 1200 |
| TGG ATG AAT TTA GCT GAG AAA ATT CCT CAA AGC CAG TAT GAT GTT GTG<br>Trp Met Asn Leu Ala Glu Lys Ile Pro Gln Ser Gln Tyr Asp Val Val<br>                    405                     410                     415 | | 1248 |
| AGT GAT CAT GTT AGC AAA GTT ACT TTT TTC AAT CTG AAT GAA ACC AAA<br>Ser Asp His Val Ser Lys Val Thr Phe Phe Asn Leu Asn Glu Thr Lys<br>            420                     425                     430 | | 1296 |
| CCT CGA GGA AAG TTT ACC TAT GAT GCA GTG TAC TGC TGC AAT GAA CAT<br>Pro Arg Gly Lys Phe Thr Tyr Asp Ala Val Tyr Cys Cys Asn Glu His<br>                435                     440                     445 | | 1344 |
| GAA TGC CAT CAT CGC TAT GCT GAA TTA TAT GTG ATT GAT GTC AAT ATC<br>Glu Cys His His Arg Tyr Ala Glu Leu Tyr Val Ile Asp Val Asn Ile<br>    450                     455                     460 | | 1392 |
| AAT ATC TCA TGT GAA ACT GAT GGG TAC TTA ACT AAA ATG ACT TGC AGA<br>Asn Ile Ser Cys Glu Thr Asp Gly Tyr Leu Thr Lys Met Thr Cys Arg<br>465                     470                     475                 480 | | 1440 |
| TGG TCA ACC AGT ACA ATC CAG TCA CTT GCG GAA AGC ACT TTG CAA TTG<br>Trp Ser Thr Ser Thr Ile Gln Ser Leu Ala Glu Ser Thr Leu Gln Leu<br>                    485                     490                     495 | | 1488 |
| AGG TAT CAT AGG AGC AGC CTT TAC TGT TCT GAT ATT CCA TCT ATT CAT<br>Arg Tyr His Arg Ser Ser Leu Tyr Cys Ser Asp Ile Pro Ser Ile His<br>            500                     505                     510 | | 1536 |
| CCC ATA TCT GAG CCC AAA GAT TGC TAT TTG CAG AGT GAT GGT TTT TAT<br>Pro Ile Ser Glu Pro Lys Asp Cys Tyr Leu Gln Ser Asp Gly Phe Tyr<br>                515                     520                     525 | | 1584 |
| GAA TGC ATT TTC CAG CCA ATC TTC CTA TTA TCT GGC TAC ACA ATG TGG<br>Glu Cys Ile Phe Gln Pro Ile Phe Leu Leu Ser Gly Tyr Thr Met Trp<br>    530                     535                     540 | | 1632 |
| ATT AGG ATC AAT CAC TCT CTA GGT TCA CTT GAC TCT CCA CCA ACA TGT<br>Ile Arg Ile Asn His Ser Leu Gly Ser Leu Asp Ser Pro Pro Thr Cys<br>545                     550                     555                 560 | | 1680 |
| GTC CTT CCT GAT TCT GTG GTG AAG CCA CTG CCT CCA TCC AGT GTG AAA<br>Val Leu Pro Asp Ser Val Val Lys Pro Leu Pro Pro Ser Ser Val Lys<br>                    565                     570                     575 | | 1728 |
| CGA GAA ATT ACT ATA AAC ATT GGA TTA TTG AAA ATA TCT TGG GAA AAG<br>Arg Glu Ile Thr Ile Asn Ile Gly Leu Leu Lys Ile Ser Trp Glu Lys<br>            580                     585                     590 | | 1776 |
| CCA GTC TTT CCA GAG AAT AAC CTT CAA TTC CAG ATT CGC TAT GGT TTA<br>Pro Val Phe Pro Glu Asn Asn Leu Gln Phe Gln Ile Arg Tyr Gly Leu<br>                595                     600                     605 | | 1824 |
| AGT GGA AAA GAA GTA CAA TGG AAG ATG TAT GAG GTT TAT GAT CGA AAA<br>Ser Gly Lys Glu Val Gln Trp Lys Met Tyr Glu Val Tyr Asp Arg Lys<br>    610                     615                     620 | | 1872 |
| TCA AAA TCT GTC AGT CTC CCA GTT CCA GAC TTG TGT GCA GTC TAT GCT | | 1920 |

```
Ser Lys Ser Val Ser Leu Pro Val Pro Asp Leu Cys Ala Val Tyr Ala
625             630             635             640

GTT CAG GTG CGC TGT AAG AGG CTA GAT GGA CTG GGA TAT TGG AGT AAT    1968
Val Gln Val Arg Cys Lys Arg Leu Asp Gly Leu Gly Tyr Trp Ser Asn
                645             650             655

TGG AGC AAT CCA GCC TAC ACA GTT GTC ATG GAT ATA AAA GTT CCT ATG    2016
Trp Ser Asn Pro Ala Tyr Thr Val Val Met Asp Ile Lys Val Pro Met
            660             665             670

AGA GGA CCT GAA TTT TGG AGA ATA ATT AAT GGA GAT ACT ATG AAA AAG    2064
Arg Gly Pro Glu Phe Trp Arg Ile Ile Asn Gly Asp Thr Met Lys Lys
        675             680             685

GAG AAA AAT GTC ACT TTA CTT TGG AAG CCC CTG ATG AAA AAT GAC TCA    2112
Glu Lys Asn Val Thr Leu Leu Trp Lys Pro Leu Met Lys Asn Asp Ser
    690             695             700

TTG TGC AGT GTT CAG AGA TAT GTG ATA AAC CAT CAT ACT TCC TGC AAT    2160
Leu Cys Ser Val Gln Arg Tyr Val Ile Asn His His Thr Ser Cys Asn
705             710             715             720

GGA ACA TGG TCA GAA GAT GTG GGA AAT CAC ACG AAA TTC ACT TTC CTG    2208
Gly Thr Trp Ser Glu Asp Val Gly Asn His Thr Lys Phe Thr Phe Leu
                725             730             735

TGG ACA GAG CAA GCA CAT ACT GTT ACG GTT CTG GCC ATC AAT TCA ATT    2256
Trp Thr Glu Gln Ala His Thr Val Thr Val Leu Ala Ile Asn Ser Ile
            740             745             750

GGT GCT TCT GTT GCA AAT TTT AAT TTA ACC TTT TCA TGG CCT ATG AGC    2304
Gly Ala Ser Val Ala Asn Phe Asn Leu Thr Phe Ser Trp Pro Met Ser
        755             760             765

AAA GTA AAT ATC GTG CAG TCA CTC AGT GCT TAT CCT TTA AAC AGC AGT    2352
Lys Val Asn Ile Val Gln Ser Leu Ser Ala Tyr Pro Leu Asn Ser Ser
    770             775             780

TGT GTG ATT GTT TCC TGG ATA CTA TCA CCC AGT GAT TAC AAG CTA ATG    2400
Cys Val Ile Val Ser Trp Ile Leu Ser Pro Ser Asp Tyr Lys Leu Met
785             790             795             800

TAT TTT ATT ATT GAG TGG AAA AAT CTT AAT GAA GAT GGT GAA ATA AAA    2448
Tyr Phe Ile Ile Glu Trp Lys Asn Leu Asn Glu Asp Gly Glu Ile Lys
                805             810             815

TGG CTT AGA ATC TCT TCA TCT GTT AAG AAG TAT TAT ATC CAT GAT CAT    2496
Trp Leu Arg Ile Ser Ser Ser Val Lys Lys Tyr Tyr Ile His Asp His
            820             825             830

TTT ATC CCC ATT GAG AAG TAC CAG TTC AGT CTT TAC CCA ATA TTT ATG    2544
Phe Ile Pro Ile Glu Lys Tyr Gln Phe Ser Leu Tyr Pro Ile Phe Met
        835             840             845

GAA GGA GTG GGA AAA CCA AAG ATA ATT AAT AGT TTC ACT CAA GAT GAT    2592
Glu Gly Val Gly Lys Pro Lys Ile Ile Asn Ser Phe Thr Gln Asp Asp
    850             855             860

ATT GAA AAA CAC CAG AGT GAT GCA GGT TTA TAT GTA ATT GTG CCA GTA    2640
Ile Glu Lys His Gln Ser Asp Ala Gly Leu Tyr Val Ile Val Pro Val
865             870             875             880

ATT ATT TCC TCT TCC ATC TTA TTG CTT GGA ACA TTA TTA ATA TCA CAC    2688
Ile Ile Ser Ser Ser Ile Leu Leu Leu Gly Thr Leu Leu Ile Ser His
                885             890             895

CAA AGA ATG AAA AAG CTA TTT TGG GAA GAT GTT CCG AAC CCC AAG AAT    2736
Gln Arg Met Lys Lys Leu Phe Trp Glu Asp Val Pro Asn Pro Lys Asn
            900             905             910

TGT TCC TGG GCA CAA GGA CTT AAT TTT CAG AAG AGA ACG GAC ATT CTT    2784
Cys Ser Trp Ala Gln Gly Leu Asn Phe Gln Lys Arg Thr Asp Ile Leu
        915             920             925

TGA AGT CTA ATC ATG ATC ACT ACA GAT GAA CCC AAT GTG CCA ACT TCC    2832
Xaa Ser Leu Ile Met Ile Thr Thr Asp Glu Pro Asn Val Pro Thr Ser
    930             935             940
```

```
CAA CAG TCT ATA GAG TAT TAG AAG ATT TTT ACA TTC TGA AGA AGG        2877
Glu Gln Ser Ile Glu Tyr Xaa Lys Ile Phe Thr Phe Xaa Arg Arg
945                 950                 955
```

(2) INFORMATION FOR SEQ ID NO: 2:

(i) SEQUENCE CHARACTERISTICS:
        (A) LENGTH: 29 amino acids
        (B) TYPE: amino acid
        (D) TOPOLOGY: linear (ii) MOLECULE TYPE: protein (xi) SEQUENCE DESCRIPTION: SEQ ID NO: 2:

```
Ala Arg Ala Thr Gln Val Pro Glu Pro Arg Pro Ala Pro Ile Ser Ala
1               5                  10                  15

Phe Gly Arg Val Gly Pro Pro Asp Gln Gly Val Leu Leu
            20                  25
```

(2) INFORMATION FOR SEQ ID NO: 3:

(i) SEQUENCE CHARACTERISTICS:
        (A) LENGTH: 898 amino acids
        (B) TYPE: amino acid
        (D) TOPOLOGY: linear (ii) MOLECULE TYPE: protein (xi) SEQUENCE DESCRIPTION: SEQ ID NO: 3:

```
Ser Lys Met Ile Cys Gln Lys Phe Cys Val Val Leu Leu His Trp Glu
1               5                  10                  15

Phe Ile Tyr Val Ile Thr Ala Phe Asn Leu Ser Tyr Pro Ile Thr Pro
                20                  25                  30

Trp Arg Phe Lys Leu Ser Cys Met Pro Pro Asn Ser Thr Tyr Asp Tyr
                35                  40                  45

Phe Leu Leu Pro Ala Gly Leu Ser Lys Asn Thr Ser Asn Ser Asn Gly
        50                  55                  60

His Tyr Glu Thr Ala Val Glu Pro Lys Phe Asn Ser Ser Gly Thr His
65                  70                  75                  80

Phe Ser Asn Leu Ser Lys Ala Thr Phe His Cys Cys Phe Arg Ser Glu
                85                  90                  95

Gln Asp Arg Asn Cys Ser Leu Cys Ala Asp Asn Ile Glu Gly Arg Thr
                100                 105                 110

Phe Val Ser Thr Val Asn Ser Leu Val Phe Gln Gln Ile Asp Ala Asn
            115                 120                 125

Trp Asn Ile Gln Cys Trp Leu Lys Gly Asp Leu Lys Leu Phe Ile Cys
        130                 135                 140

Tyr Val Glu Ser Leu Phe Lys Asn Leu Phe Arg Asn Tyr Asn Tyr Lys
145                 150                 155                 160

Val His Leu Leu Tyr Val Leu Pro Glu Val Leu Glu Asp Ser Pro Leu
                165                 170                 175

Val Pro Gln Lys Gly Ser Phe Gln Met Val His Cys Asn Cys Ser Val
            180                 185                 190

His Glu Cys Cys Glu Cys Leu Val Pro Val Pro Thr Ala Lys Leu Asn
            195                 200                 205

Asp Thr Leu Leu Met Cys Leu Lys Ile Thr Ser Gly Gly Val Ile Phe
        210                 215                 220

Arg Ser Pro Leu Met Ser Val Gln Pro Ile Asn Met Val Lys Pro Asp
225                 230                 235                 240
```

-continued

```
Pro Pro Leu Gly Leu His Met Glu Ile Thr Asp Asp Gly Asn Leu Lys
            245                 250                 255

Ile Ser Trp Ser Ser Pro Leu Val Pro Phe Pro Leu Gln Tyr Gln
            260                 265                 270

Val Lys Tyr Ser Glu Asn Ser Thr Thr Val Ile Arg Glu Ala Asp Lys
            275                 280                 285

Ile Val Ser Ala Thr Ser Leu Leu Val Asp Ser Ile Leu Pro Gly Ser
            290                 295                 300

Ser Tyr Glu Val Gln Val Arg Gly Lys Arg Leu Asp Gly Pro Gly Ile
305                 310                 315                 320

Trp Ser Asp Trp Ser Thr Pro Arg Val Phe Thr Thr Gln Asp Val Ile
                325                 330                 335

Tyr Phe Pro Pro Lys Ile Leu Thr Ser Val Gly Ser Asn Val Ser Phe
                340                 345                 350

His Cys Ile Tyr Lys Lys Glu Asn Lys Ile Val Pro Ser Lys Glu Ile
                355                 360                 365

Val Trp Trp Met Asn Leu Ala Glu Lys Ile Pro Gln Ser Gln Tyr Asp
    370                 375                 380

Val Val Ser Asp His Val Ser Lys Val Thr Phe Phe Asn Leu Asn Glu
385                 390                 395                 400

Thr Lys Pro Arg Gly Lys Phe Thr Tyr Asp Ala Val Tyr Cys Cys Asn
                405                 410                 415

Glu His Glu Cys His His Arg Tyr Ala Glu Leu Tyr Val Ile Asp Val
                420                 425                 430

Asn Ile Asn Ile Ser Cys Glu Thr Asp Gly Tyr Leu Thr Lys Met Thr
                435                 440                 445

Cys Arg Trp Ser Thr Ser Thr Ile Gln Ser Leu Ala Glu Ser Thr Leu
    450                 455                 460

Gln Leu Arg Tyr His Arg Ser Ser Leu Tyr Cys Ser Asp Ile Pro Ser
465                 470                 475                 480

Ile His Pro Ile Ser Glu Pro Lys Asp Cys Tyr Leu Gln Ser Asp Gly
                485                 490                 495

Phe Tyr Glu Cys Ile Phe Gln Pro Ile Phe Leu Leu Ser Gly Tyr Thr
                500                 505                 510

Met Trp Ile Arg Ile Asn His Ser Leu Gly Ser Leu Asp Ser Pro Pro
                515                 520                 525

Thr Cys Val Leu Pro Asp Ser Val Val Lys Pro Leu Pro Pro Ser Ser
    530                 535                 540

Val Lys Arg Glu Ile Thr Ile Asn Ile Gly Leu Leu Lys Ile Ser Trp
545                 550                 555                 560

Glu Lys Pro Val Phe Pro Glu Asn Asn Leu Gln Phe Gln Ile Arg Tyr
                565                 570                 575

Gly Leu Ser Gly Lys Glu Val Gln Trp Lys Met Tyr Glu Val Tyr Asp
                580                 585                 590

Arg Lys Ser Lys Ser Val Ser Leu Pro Val Pro Asp Leu Cys Ala Val
                595                 600                 605

Tyr Ala Val Gln Val Arg Cys Lys Arg Leu Asp Gly Leu Gly Tyr Trp
                610                 615                 620

Ser Asn Trp Ser Asn Pro Ala Tyr Thr Val Val Met Asp Ile Lys Val
625                 630                 635                 640

Pro Met Arg Gly Pro Glu Phe Trp Arg Ile Ile Asn Gly Asp Thr Met
                645                 650                 655

Lys Lys Glu Lys Asn Val Thr Leu Leu Trp Lys Pro Leu Met Lys Asn
```

```
                   660               665                 670
Asp Ser Leu Cys Ser Val Gln Arg Tyr Val Ile Asn His His Thr Ser
            675                 680                 685
Cys Asn Gly Thr Trp Ser Glu Asp Val Gly Asn His Thr Lys Phe Thr
            690                 695                 700
Phe Leu Trp Thr Glu Gln Ala His Thr Val Thr Val Leu Ala Ile Asn
705                 710                 715                 720
Ser Ile Gly Ala Ser Val Ala Asn Phe Asn Leu Thr Phe Ser Trp Pro
                725                 730                 735
Met Ser Lys Val Asn Ile Val Gln Ser Leu Ser Ala Tyr Pro Leu Asn
            740                 745                 750
Ser Ser Cys Val Ile Val Ser Trp Ile Leu Ser Pro Ser Asp Tyr Lys
            755                 760                 765
Leu Met Tyr Phe Ile Ile Glu Trp Lys Asn Leu Asn Glu Asp Gly Glu
            770                 775                 780
Ile Lys Trp Leu Arg Ile Ser Ser Val Lys Lys Tyr Tyr Ile His
785                 790                 795                 800
Asp His Phe Ile Pro Ile Glu Lys Tyr Gln Phe Ser Leu Tyr Pro Ile
                805                 810                 815
Phe Met Glu Gly Val Gly Lys Pro Lys Ile Ile Asn Ser Phe Thr Gln
                820                 825                 830
Asp Asp Ile Glu Lys His Gln Ser Asp Ala Gly Leu Tyr Val Ile Val
            835                 840                 845
Pro Val Ile Ile Ser Ser Ile Leu Leu Leu Gly Thr Leu Leu Ile
            850                 855                 860
Ser His Gln Arg Met Lys Lys Leu Phe Trp Glu Asp Val Pro Asn Pro
865                 870                 875                 880
Lys Asn Cys Ser Trp Ala Gln Gly Pro Asn Phe Gln Lys Arg Thr Asp
                885                 890                 895
Ile Leu (2) INFORMATION FOR SEQ ID NO: 4:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO: 4:

Ser Leu Ile Met Ile Thr Thr Asp Glu Pro Asn Val Pro Thr Ser Gln Gln
1               5                   10                  15

Ser Ile Glu Tyr
        20

(2) INFORMATION FOR SEQ ID NO: 5:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 5:

Lys Ile Phe Thr Phe
1           5
```